United States Patent
Ungemach et al.

(10) Patent No.: US 9,889,282 B2
(45) Date of Patent: Feb. 13, 2018

(54) IMPLEMENT FOR A SKIN TREATMENT DEVICE

(71) Applicant: Braun GmbH, Kronberg (DE)

(72) Inventors: Christof Ungemach, Frankfurt am Main (DE); Michael Maichel, Frankfurt am Main (DE); Ulrich Stoerkel, Bad Nauheim (DE); Jochen Kawerau, Kronberg (DE); Frank Roland Gliemroth, Schwalbach (DE)

(73) Assignee: Braun GmbH, Kronberg (DE)

( * ) Notice: Subject to any disclaimer, the term of this patent is extended or adjusted under 35 U.S.C. 154(b) by 471 days.

(21) Appl. No.: 13/964,177

(22) Filed: Aug. 12, 2013

(65) Prior Publication Data
US 2014/0058300 A1 Feb. 27, 2014

(30) Foreign Application Priority Data

Aug. 21, 2012 (EP) ..................... 12181134
May 8, 2013 (EP) ..................... 13167040

(51) Int. Cl.
| | |
|---|---|
| *A61H 7/00* | (2006.01) |
| *A61M 35/00* | (2006.01) |
| *A46B 9/02* | (2006.01) |
| *A46B 9/06* | (2006.01) |
| *A46B 13/00* | (2006.01) |

(52) U.S. Cl.
CPC .............. *A61M 35/003* (2013.01); *A46B 9/02* (2013.01); *A46B 9/028* (2013.01); *A46B 9/06* (2013.01); *A46B 13/008* (2013.01); *A61H 7/005* (2013.01); *A46B 2200/102* (2013.01); *A46B 2200/1006* (2013.01); *A61H 2201/1685* (2013.01); *F04C 2270/0421* (2013.01)

(58) Field of Classification Search
CPC ........... A61H 7/005; A61H 2201/1685; A61M 35/003; A46B 9/02; A46B 9/028; A46B 9/06; A46B 13/008; A46B 2200/102; A46B 2200/1006
See application file for complete search history.

(56) References Cited

U.S. PATENT DOCUMENTS

| | | | |
|---|---|---|---|
| 2,714,788 | A | 8/1955 | Di Giovanna |
| 6,569,170 | B1 | 5/2003 | Kellogg |
| 6,726,789 | B1 | 4/2004 | Weihrauch |
| 8,256,437 | B2 | 9/2012 | Gueret |

(Continued)

FOREIGN PATENT DOCUMENTS

| | | |
|---|---|---|
| DE | 20117673 U1 | 3/2002 |
| EP | 2253242 A1 | 11/2010 |

(Continued)

OTHER PUBLICATIONS

European Search Report dated Dec. 10, 2012, 9 pages.
European Search Report dated Oct. 28, 2013, 7 pages.

*Primary Examiner* — Quang D Thanh
(74) *Attorney, Agent, or Firm* — Ronald T. Sia; Kevin C. Johnson; Steven W. Miller

(57) ABSTRACT

A brush implement for the use with a skin treatment device, the brush implement having bristles of a first type and bristles of a second type, wherein the bristles of the first type are longer than the bristles of the second type and are positioned closer to the outer contour of the brush implement and the bristles form at least three distinguishable sectors.

18 Claims, 5 Drawing Sheets

(56) References Cited

U.S. PATENT DOCUMENTS

| | | |
|---|---|---|
| 2004/0112400 A1 | 6/2004 | Kurek |
| 2005/0278876 A1* | 12/2005 | Roth ............... A46B 13/06 |
| | | 15/28 |
| 2009/0177125 A1* | 7/2009 | Pilcher ........... A46B 15/0034 |
| | | 601/18 |
| 2010/0222719 A1 | 9/2010 | Cowe et al. |
| 2011/0184499 A1* | 7/2011 | Radi ................. A61H 7/005 |
| | | 607/88 |
| 2012/0204369 A1 | 8/2012 | Watanabe et al. |
| 2012/0233798 A1 | 9/2012 | Brewer et al. |
| 2013/0023805 A1 | 1/2013 | Ungemach et al. |

FOREIGN PATENT DOCUMENTS

| | | | |
|---|---|---|---|
| EP | 2443958 A1 | 4/2012 | |
| EP | 2 478 884 A1 * | 7/2012 | ........... A61H 7/00 |
| FR | 940675 A | 12/1948 | |
| JP | 2007/135964 | 6/2007 | |
| WO | WO 8000787 A1 | 5/1980 | |
| WO | WO-2001/56529 | 8/2001 | |
| WO | WO 2008098646 A1 | 8/2008 | |

\* cited by examiner

IMPLEMENT FOR A SKIN TREATMENT DEVICE

FIELD OF THE INVENTION

The present invention is concerned with a skin treatment device for professional and private use. The device is used for achieving cosmetic or well-being benefits, for example it can be used for massaging or for cleansing and refreshing the skin or for applying a cosmetic composition. A particular focus is to provide an improved brush implement for such a skin treatment device.

BACKGROUND OF THE INVENTION

A wide variety of cosmetic moisturizing and other agents is available to meet the interest in having a clean, healthy and good-looking skin and face. Relative to these offers of the cosmetic industry, the use of skin care appliances and devices is slightly more limited, but many efforts have also been made in this field.

U.S. Pat. No. 2,714,788 discloses a device for removing hair, which device comprises an electric motor, a holder for an abrasive pad and an abrasive pad. This device is meant to remove hairs from the skin of, for example, the legs by means of abrasion.

EP 1 429 670 A2 discloses an ultrasonic cleaner comprising a handle and a brush positioned at the proximal end off the handle. The cleaner further comprises an ultrasonic vibrator attached to the brush. A battery positioned within the hollow interior of the handle provides power to the ultrasonic vibrator. Ultrasonic vibration is transmitted from the vibrator through the brush and to its bristles. The cleaner can hence be used for skin cleaning.

WO 2010/100527 A1 discloses an appliance for facial care. The facial appliance comprises a tubular body and axially extending from the tubular body a so-called facial puck. This facial puck comprises a facial implement rotatable about a shaft and a sub assembly linked to the shaft. This sub assembly includes a spinner mounted for rotation about an axis extending from the tubular body. The spinner comprises opposing, radially extending, resiliently biased release fingers. These release fingers detachably mount the applicator implement (e.g. the facial implement) for rotation with the spinner. The spinner is mounted to the main gear by slip bearings.

It is an objective of the present invention to provide an improved implement for a skin treatment device. It is further objective to provide a versatile skin treatment device. A skin treatment device in accordance with the present invention should be efficient in applying a cosmetic composition. This should be done with a skin treatment device of limited power.

SUMMARY OF THE INVENTION

The present invention is concerned with a skin treatment device for professional and private use.

In accordance with an aspect of the present disclosure, a brush implement for the use with a skin treatment device is provided, the brush implement comprising bristles of a first type and bristles of a second type, wherein the bristles of the first type are longer than the bristles of the second type and are positioned closer to the outer contour of the brush implement and the bristles form at least three distinguishable sectors.

DETAILED DESCRIPTION OF THE INVENTION

Figure 1:
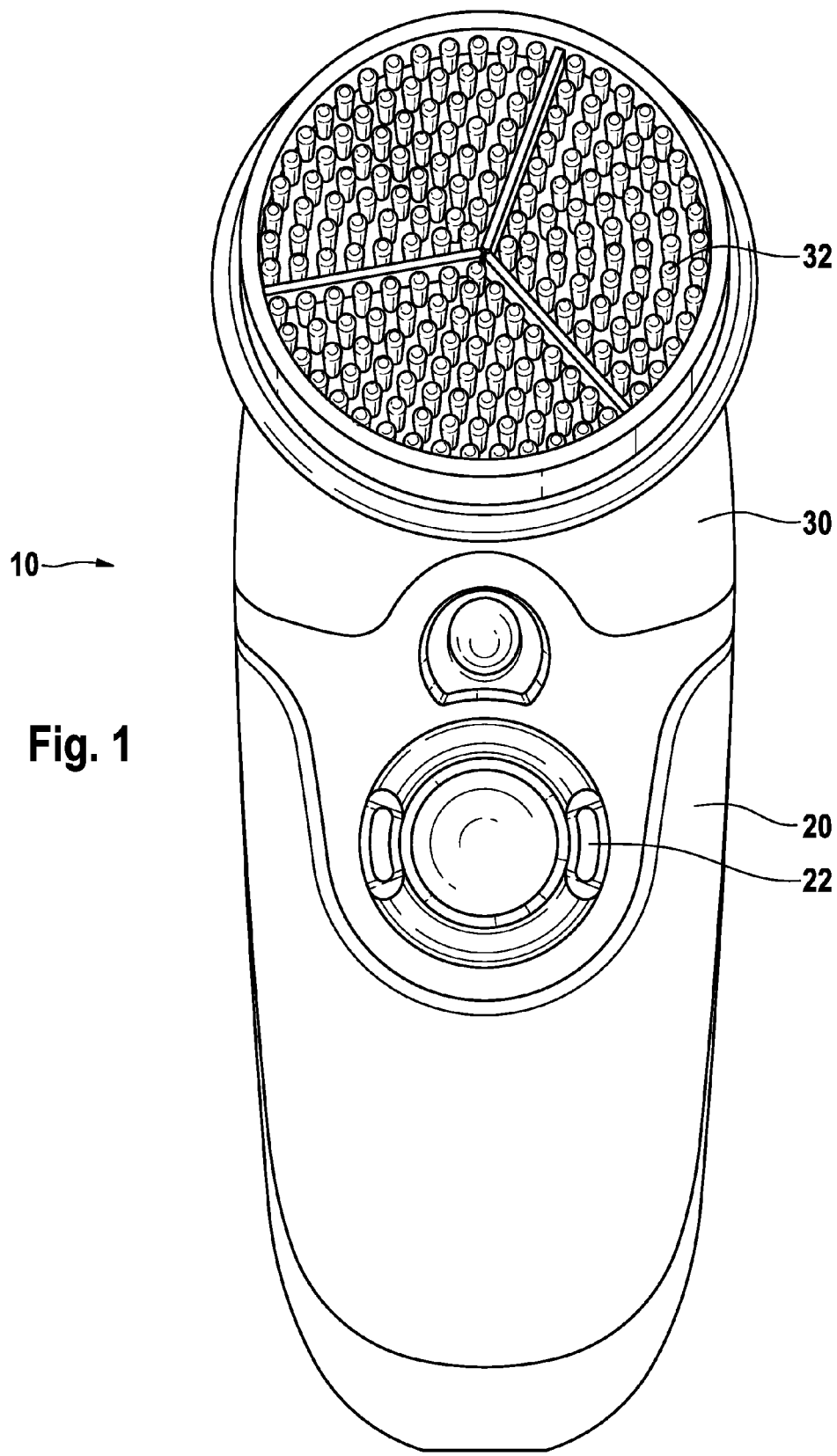
FIG. 1 shows a plain view onto a skin treatment device according to the present disclosure.

A skin treatment device in accordance with the present disclosure comprises a drive unit and a brush implement. The skin treatment device may also be provided as a kit with two, three or more implements, at least one of these implements being a brush implement. At a given time one implement can be used with the drive unit. Additionally or alternatively, the drive unit may also be adapted to operate two or more implements at the same time. However, a drive unit which can operate one implement at the time has been found useful. The brush implement therefore may be detachably mounted to the drive unit. A brush implement which is detachably mounted and which is hence attachable and detachable from the drive unit can also be referred to as an attachment. Such an attachment can comprise units further skin treatment elements. The attachment may also comprise a gear box or one or more force transmission elements.

The drive unit can be hand operated or motor operated. Often the drive unit is operated by an electric motor. This electric motor can be operated by a battery, for example a rechargeable battery. Drive units needing a cable for contact with the power supply while being operated can also be useful.

The present disclosure is in particular concerned with a brush implement for the use with the skin treatment device. The brush implement can either be integral with the skin treatment device or detachable from the skin treatment device. A detachable brush implement can for example take the form of an attachment for a skin treatment device or in particular for its drive unit. As basic components the brush implement can comprise a brush mounted on a brush chassis. The skin treatment device is a device for treating the outer skin of the body of a user.

It has been found useful to equip such a device with two, three or more different types of bristles (in the following, "first type of bristles" and "first bristle" etc. are interchangeably used, while the term "bristle" shall mean a bristle of any type). Bristles are understood as belonging to a different type, if they are different in at least one relevant physical property. Such a property may be the length, the diameter of the bristles, their material, at least as far as the color of the material is concerned, their rigidity, flexibility, or the like. It has been found useful to provide the different types of bristle with different lengths. The term length is to be understood as the efficient length defining when a bristle touches the skin relative to the position of the skin treatment device, or in other words, the length of a bristle is the distance between the mounting surface on which the bristle is mounted and the free end of the bristle.

It has been found useful to have an arrangement of the bristles in different sectors. Each sector of the brush implement can comprise two or three or more bristles of different types. It is found useful that the brush implement comprises three, four or more sectors in symmetrical arrangement. For example the sectors may have a rotational symmetry (i.e. one sector can be essentially exactly overlaid on another sector by rotating the sector around a symmetry axis, e.g. in case of three sectors, each one of the sectors can essentially exactly overlaid onto another sector by a 120 degree rotation around the symmetry axis, in case of four sectors by a 90 degree rotation etc.). It is hence useful that each sector has the same arrangement of bristles.

It has been found useful that the outermost bristles, which are the bristles defining the outer contour of the brush, are of one type. The bristles of the first type may form the outer contour of the brush. The bristles of the first type may have a greater length than the bristles of the second type. In some embodiments, the bristles of the first type and/or the bristles of the second type may have a circular cross section. In some embodiments, the bristles of the first type have a smaller diameter than the bristles of the second type. In some embodiments, the bristles of the first type may be arranged with a shorter distance to each other than the bristles of the second type.

It has been found useful to provide a skin treatment device, which provides a decoupling mechanism for the brush implement. Such decoupling mechanism allows replacing one brush implement by another brush implement. Hence, the decoupling mechanism makes the brush implement detachable. However, a yet more useful mechanism allows decoupling the brush implement from the driving forces of the drive unit. To this end, a decoupling (directly or indirectly) from the drive shaft of a drive unit is useful. This can avoid exerting too much force either onto the drive unit and/or onto the skin of a user.

It is useful to provide the brush implement with split end filaments. Such filaments can have a single shaft but several ends, for example three or four ends. Such filaments can be used for example to form bristles of the second type or bristles of a third type The brush implement also can comprise a rotary support element. The rotary support element can have a variety of useful forms, and should be linked to the drive unit as to impart a rotation to the skin treatment element. The rotary support element can for example have a planar surface perpendicular to the rotating axis, which can support the skin treatment element. The rotary support element further can have some protrusions. The protrusions can have a variety of suitable forms, for example they can be of a rounded or a squared form, the protrusions for example can take the form of noses or pyramids or the like. Protrusions of triangular cross-sections have been found useful. The respective protrusions can be used for mechanically linking the skin treatment element to the rotary support element. For this purpose, the skin treatment element can comprise a multitude of recesses. These recesses can cooperate with the protrusions of the rotary support element. To this end, it is useful that the form of the recesses is optimized for receiving the protrusions. Therefore, the recesses can also be of an essentially rounded or squared form. For example, recesses of triangular cross-section are useful for receiving protrusions of triangular cross-section. The recesses can form part of a toothed ring. It is useful, that the recesses of the rotary support element are facing towards the axis of rotation of the rotary support element.

The protrusions can be provided in the form of latches. It is useful that the protrusions are provided with spring loaded pins. The biasing force of the springs together with the form of the protrusions and recesses define the force threshold at which in response to an outer force the disengagement position is assumed. Hence, this threshold can be easily selected for a given device and the expected usage conditions.

Irrespective of the particular mechanical setup, it is beneficial, that the protrusions can be brought into engagement position with the recesses and, while the chassis is supported by the rotary support element, into a disengagement position with the recesses.

In the engagement position a force can be transmitted to the chassis for inducing a rotational movement. The cooperation of the protrusions and recesses is such, that a low vibration and low noise operation is achieved.

In disengagement position no or essentially no such force is transmitted. Hence the chassis can move freely about the axis of rotation in the disengagement position, but continues to be supported and hence held in position by the rotary support element. Therefore, in the disengagement position, mechanical parts of the drive unit or a gear box cannot be damaged by any force exerted upon the chassis beyond the force required for the disengagement position to be assumed.

FIG. 1 shows a skin treatment device 10 with its essential elements according to the present disclosure. The device 10 comprises a drive unit 20. The drive unit can comprise a motor which will typically provide a rotational or vibrational movement to some output device. The motor will typically be an electrical motor which can be battery operated, preferably by a rechargeable battery. The drive unit 20 will comprise a switch 22, for turning the unit on or off and/or making other selections of an operation mode.

An attachment 30 (here, a brush implement is shown) can be connected to the drive unit 20. A variety of suitable connectors are well-known, often a positive fitting is useful. Other attachments can be connected to the drive unit, for example attachment 30 can serve as a first attachment, and a further attachment can serve as a second attachment, which can also be connected to the same drive unit 20. The attachment 30 as shown comprises a brush 32. The term brush is used herein broadly, to denote an implement, which can comprise conventional bristles of a variety of materials, as known from other areas. The brush can also comprise rubber implements, which could have bristle form or which could also have the form of bars or ligaments. The brush 32 will typically have a circular outer shape, but could also have other shapes.

Figure 2:
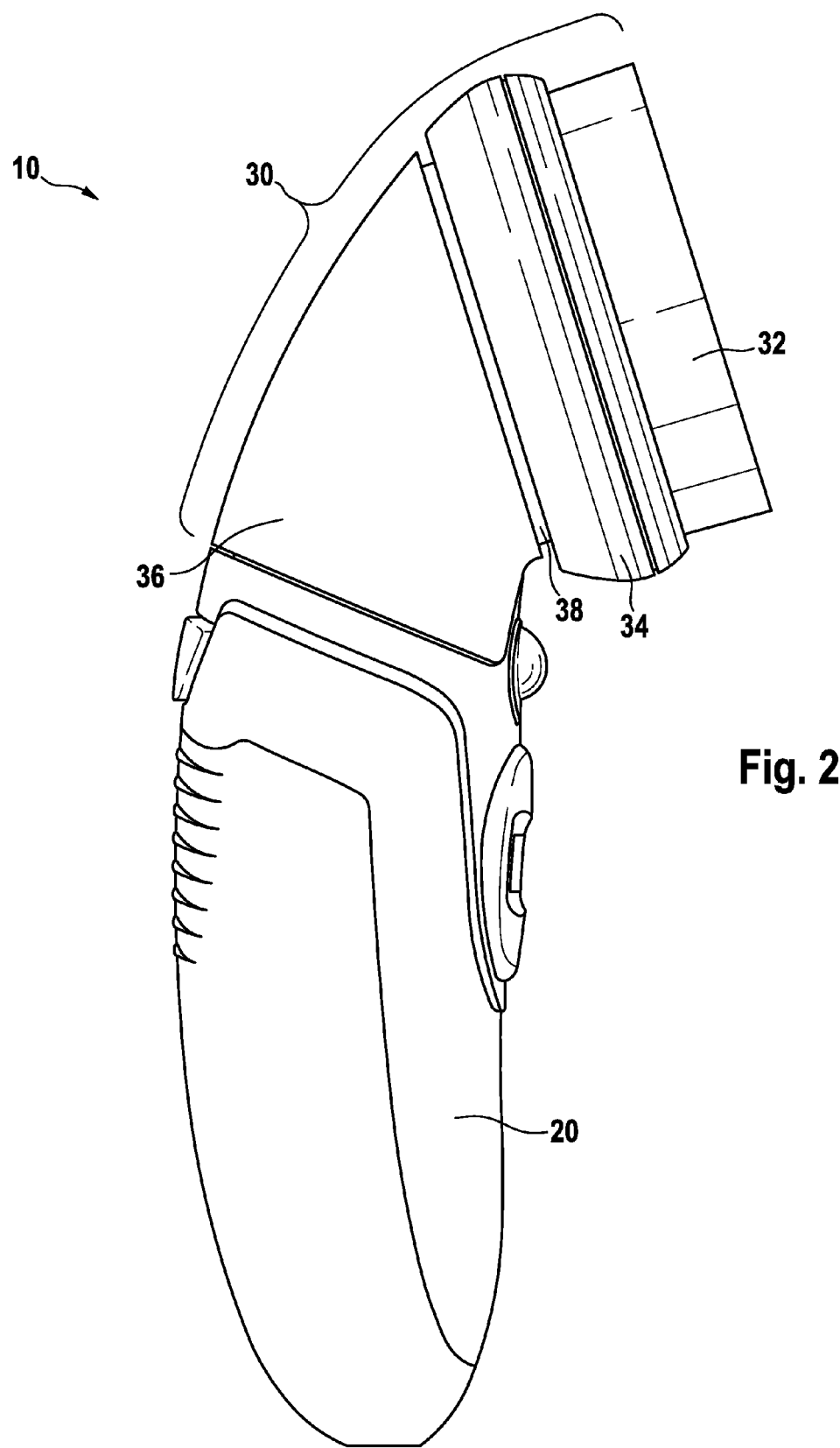
FIG. 2 shows a side view of the skin treatment device of FIG. 1.

FIG. 2 shows the same device 10 in a side view. From the side view it is clear that the main axis of the drive unit 20 and the rotational axis of the brush 32 are tilted towards each other. An angle of about 110° has been found useful. Angles in the range of 90° to 135° and 100° to 120° have generally been found useful for convenient and effective handling. In this side view it can be readily seen, that the attachment 30 comprises a gear box 36, onto which the brush 32 with the brush chassis 34 is mounted. The gear box 36 is connected to the brush chassis 34 via a rotary support element 38, which is only visible in this view as a ring like structure connection brush chassis 34 to gear box 36.

Figure 3:
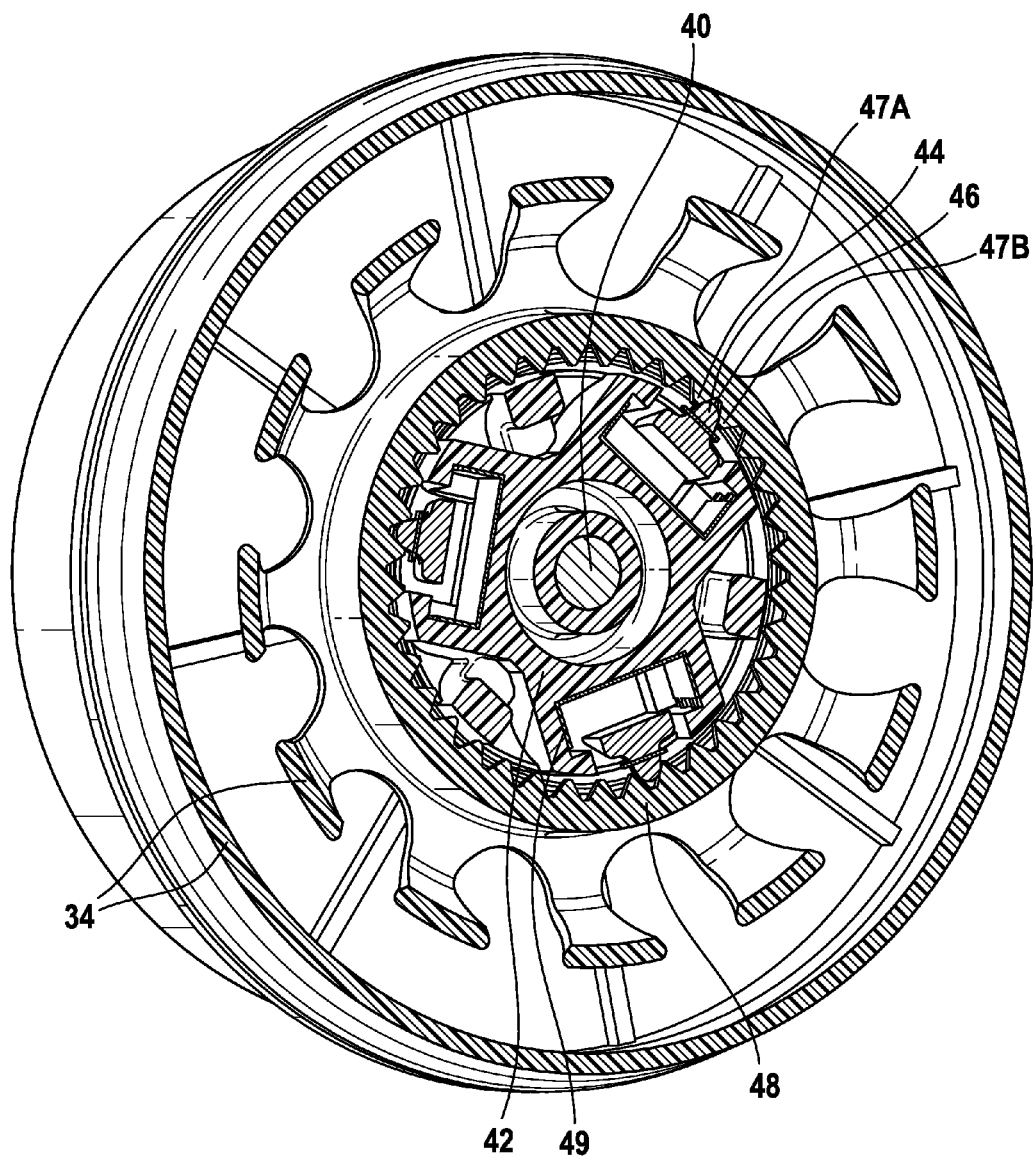
FIG. 3 shows a partially cutaway rear view onto a brush implement according to the present disclosure.

FIG. 3 provides a partially cut enlarged view of the brush chassis 34 and elements providing rotational support for the implement, which is represented here in form of a brush implement and accordingly comprises brush chassis 34. The rotational force is provided by drive shaft 40. The drive shaft 40 is mechanically connected to and supported by support plate 42. Support plate 42 comprises three latches 44.

The latches 44 are provided with noses facing away from drive axis 40. The latches 44 with their respective noses engage with triangular recesses 46 of the toothed ring 48 of the chassis 34. Representative tooth 47A and tooth 47B defining recess 46 are shown.

It is obvious from the Figure, that an engagement in many selectable positions of the latches 44 and the recesses is possible. Hence the chassis 34 can be engaged with the rotary support element 38 in various angular positions. In accordance with the present invention the angular offset of these positions is no more than 45°, preferably no more than 30° or 20° or 10° or 5°. Hence, a brush can be attached to the drive unit in many adjacent positions, such that the attachment is intuitive and convenient.

Hence, when a high tangential force is used the fit between chassis 34 and rotary support element 38 can be maintained. However, the disengagement position is assumed as the spring loaded latches disengage from their respective recesses. They can engage with one of the neighboring recesses 46, once the applied tangential force lessens and becomes insufficient for forcing the latches 44 out of the recesses.

Figure 4:
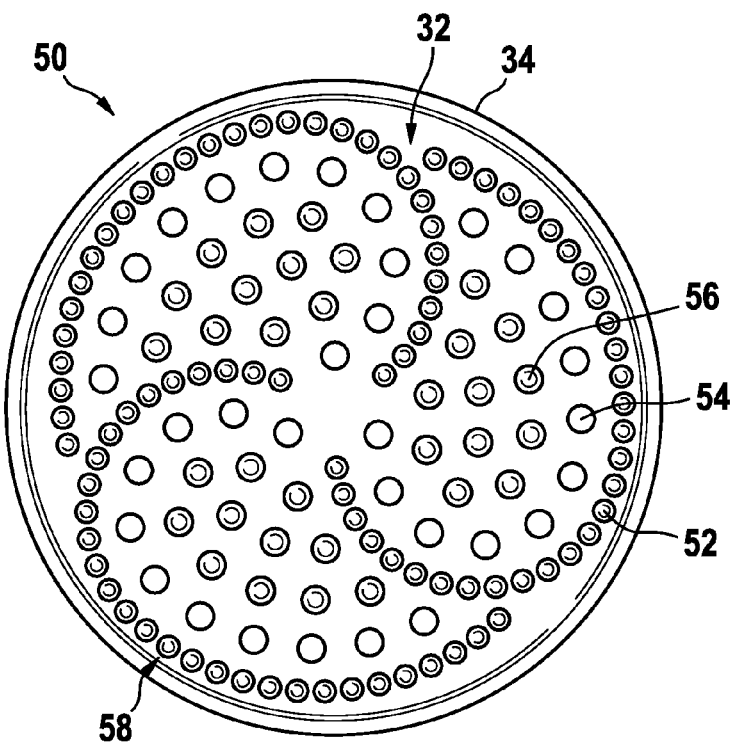
FIG. 4 shows a plain view onto a brush implement.

FIG. 4 shows a plain view onto a brush implement 50 according to the present disclosure. The brush implement 50 comprises a brush 32 supported by chassis 34. The brush implement 50 comprises a usage surface which is visible in this plane view. This brush 32 has different types of bristles 52, 54, 56. First bristles 52 are arranged on the outer circumference of the brush. Hence the brush comprises a distinct outer row of bristles, here provided by the first bristles 52.

The first bristles 52 are not only providing the outer row of bristles, but they are further providing a certain outer contour to the brush 32.

The brush head 50 comprises bristles arranged in three sectors. Each of the sectors comprises bristles of a first type 52, bristles of a second type 54, and bristles of a third type 56. The brush has trifold rotation symmetry. As mentioned above, each of the sectors and its respective bristle arrangement can be essentially exactly overlaid onto another sector and its respective bristle arrangement by a 120 degree rotation in clockwise or counter-clockwise direction around the symmetry axis originating from the centre of the brush. The first bristles 52 of each sector are arranged in a convex contour, similar to a half circle. The contour could also be described as representing a bushel form. Each of these three first bristle bushel contours originates in the center of the brush, even though the centre of the brush is here bristle-free. Within the three bushels formed by the first bristles 52 further bristles are arranged. Second bristles 54 describe a row which is essentially parallel to the row of the first bristles 52 (hence the second bristles 54 of each of the sectors also are arranged along a curved line forming bushel-like contour inside of the respective bushel contour formed by the first bristles 52). The inner area of each of the three bushels is filled with third bristles 56. The first bristles 52 are here arranged with a shorter distance to each other than the second and third bristles 54, 56 so that the bristles of the first type are arranged quite close to each other. A short distance essentially seals the inner part of the brush in use so that, e.g., during a use of the brush under a shower (i.e. when the brush is pushed against the skin), the water cannot easily penetrate into the brush and thus the rinsing of the brush is reduced and a (cosmetic) composition applied on the brush may be kept for a longer period.

As is shown in FIG. 4, the bristles of the first type 52 and the bristles of the second type 54 (optionally also the bristles of the third type) may essentially have a circular cross section and the diameter of the bristles of the first type may then be smaller than the diameter of the bristles of the second type (optionally also smaller than the diameter of the bristles of the third type). In an embodiment as shown, the diameter of the bristles of the second type and the diameter of the bristles of the third type may essentially be the same. The diameter of the bristles of the first type may be about 1.25 mm, while the diameter of the bristles of the second type (optionally also of the third type) may be about 1.8 mm (in particular measured at the level of the surface of the brush).

Figure 5:
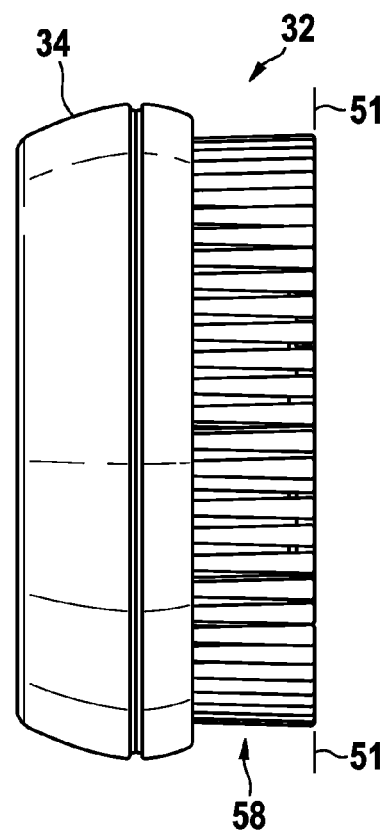
FIG. 5 shows a side view onto the same brush implement.

FIG. 5 shows a side view of the brush. Again the brush 32 is supported by chassis 34. The brush head can comprise a multitude of bristles. The outer contour 58 of the brush head is defined by only one type of bristles, in the shown embodiment these are first bristles 52. These first bristles 52 therefore also define the outer level 51 of the usage surface 52. Hence, the length of the first bristles 52 defines the point at which the brush implement makes the first contact with the skin of a user. Hence, the relatively complex structure of the brush head 50 does not appear so complex from the side view. This is an esthetic benefit which is of high value for a beauty device in the form of a skin treatment device.

Figure 6:
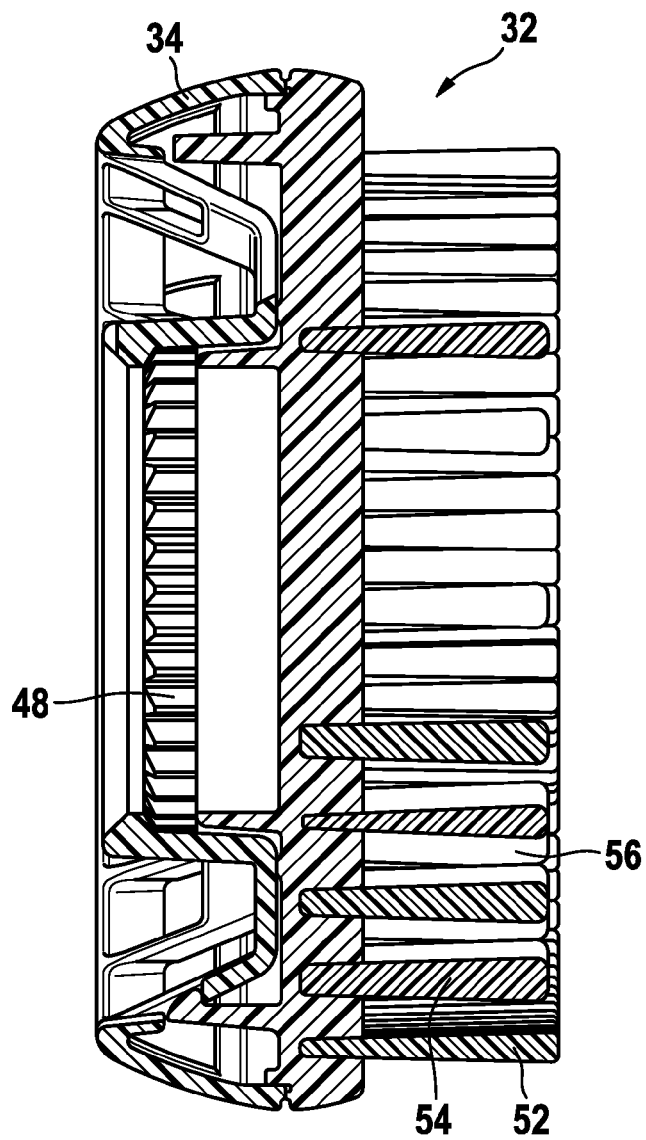
FIG. 6 shows a partially cutaway side view of the brush implement.

FIG. 6 shows a partially cutaway side view of the same implement as shown in FIGS. 4 and 5. The chassis 34 comprises a toothed ring. The toothed ring again provides a safe but also force limiting attachment to a drive unit. In this partially cutaway view, it is apparent, that the brush comprises bristles of different length. The first bristles 52 are longer than the second bristles 54 and the third bristles 56. The second bristles 54 and the third bristles 56 are chosen to be of same length.

As said before, the different types of bristles can also be chosen to be of various different length. For example the first bristles 52 are here chosen to be longer than the second bristles 54 which in turn can also be longer than the third bristles 56. In the shown embodiment, the second bristles and the third bristles have the same length.

The longer first bristles 52 define the outer contour of the brush and also separate the three sectors of the shown embodiment from each other so that a (cosmetic) composition (such as a gel or a crème) that may be applied with the shown brush is on the one hand kept inside of the brush due to the longer outer first bristles 52 arranged at a short distance (i.e. the longer bristles avoid that such a composition is squeezed to the outside) and is also kept within each of the sectors.

Figure 7:
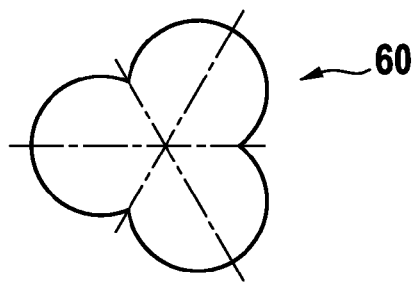
FIG. 7 shows a cross-section of one type of filament, which is useful for a brush implement in accordance with the present disclosure.

FIG. 7 shows a cross-sectional view through a filament, which is useful for providing bristles. The cross-section is perpendicular to the main axis of the filament. The cross-section is of trifold symmetry. In some sense, the filament can be understood as representing three filaments combined (or as the process may be melted together). In a production process, especially after the filament is attached to the chassis of a brush, the filament ends can be treated further. For example, a mechanical impact, such as by a not too sharp knife, can achieve that the different segments of the filament are separated (so-called flagging). Thereby, a bristle is obtained, which comprises a single shaft and three microfilaments at the top. The split end filaments may have a length of about 8.0 mm to 9.0 mm and the length of the flagging may be in the range of about 2.0 mm to 3.0 mm.

Generally, each bristle may be formed by a plurality of densely arranged filaments, where the number of filaments per bristle may lay in the range of between about 10 to 200 filaments. The filaments may be made from polyamide (e.g. PA 6.12) and each filament may have a diameter in the range of about 5 mil (about 0.127 mm) to about 6 mil (about 0.1514 mm). The diameter of each end of the split end filaments may then be about 2 mil (0.0508 mm). The split end filaments provide a higher surface area to which a (cosmetic) composition can adhere and are thus useful in holding and applying (in particular: homogeneously applying) compositions to the skin.

Alternatively, ligaments can also be used to replacing some or all of the bristles. Ligaments are elements with more volume than typical bristles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A brush implement for the use with a skin treatment device, the brush implement having an outer contour, a symmetry axis, and comprising bristles of a first type and bristles of a second type, wherein the bristles of the first type are longer than the bristles of the second type and are positioned closer to the outer contour of the brush implement than the bristles of the second type to form an outer perimeter of bristles of the first type, and the bristles of the first type and the second type form at least three distinguishable sectors, wherein the sectors each have the same arrangement of bristles and the sectors have a discrete rotation symmetry such that each of the sectors overlay onto another sector upon rotation in clockwise or counter-clockwise rotation around the symmetry axis, and wherein each sector includes a row of bristles of the first type originating adjacent a center of the brush and extending along a convex contour.

2. The brush implement according to claim 1, further comprising bristles of a third type that differ from the bristles of the first type and the bristles of the second type at least in one of the following characteristics: length, diameter, material, rigidity, or flexibility.

3. The brush implement according to claim 2, wherein the bristles of the third type have the same length as the bristles of the second type.

4. The brush implement according to claim 1, wherein each bristle is formed from a plurality of filaments.

5. The brush implement according to claim 1, wherein the outer perimeter of bristles only comprises bristles of the first type.

6. The brush implement according to claim 1, wherein at least one of the bristles of the first type and the bristles of the second type have a circular cross section.

7. The brush implement according to claim 1, wherein the bristles of the first type have a smaller diameter than the bristles of the second type.

8. The brush implement according to claim 1, comprising bristles formed by split end filaments.

9. The brush implement according to claim 2, wherein the bristles of at least one of: the first type; the second type; and the bristles of the third type are formed by split end filaments.

10. The brush implement according to claim 1, wherein the bristles of the first type are arranged with a shorter distance to each other than the bristles of the second type.

11. The brush implement according to claim 1, comprising a brush chassis, wherein the brush chassis is equipped with a coupling mechanism suitable for coupling to a skin treatment device.

12. A skin treatment device comprising a drive unit and the brush implement in accordance with claim 1 connected to the drive unit.

13. The brush implement according to claim 11, wherein the coupling mechanism comprises three latches spaced-apart from each other about an axis.

14. A brush implement for use with a skin treatment device, the brush implement comprising:
   a center of the brush implement;
   a first plurality of a first type of bristle, the first plurality of the first type of bristle forming a first row of the first type of bristle in a convex contour having a proximal end adjacent to the center of the brush implement, a distal end, and a central portion;
   a second plurality of the first type of bristle spaced apart from the first plurality of the first type of bristle, the second plurality of the first type of bristle forming a second row of the first type of bristle in a convex contour having a proximal end adjacent to the center of the brush implement, a distal end, and a central portion;
   a third plurality of the first type of bristle spaced apart from both the first and second pluralities of the first type of bristle, the third plurality of the first type of bristle forming a third row of the first type of bristle in a convex contour having a proximal end adjacent to the center of the brush implement, a distal end, and a central portion;
   a portion of bristles of the first type of bristle disposed on the brush implement forming an outer perimeter of the brush implement;
   wherein:
      the first and second rows of the first type of bristle and the outer perimeter of the first type of bristle form a first sector,
      the second and third rows of the first type of bristle and the outer perimeter of the first type of bristle form a second sector, and
      the first and third row of the first type of bristle and the outer perimeter of the first type of bristle form a third sector;
   a first plurality of a second type of bristle disposed within the first sector;

a second plurality of the second type of bristle disposed within the second sector; and a third plurality of the second type of bristle disposed within the third sector;

wherein a length of the bristle of the first type is greater than a length of the bristle of the second type.

15. The brush implement according to claim 14, wherein the first, second, and third pluralities of the second type of bristle are disposed parallel to the respective first, second, and third rows of the first type of bristle.

16. The brush implement according to claim 15, further comprising first, second, and third pluralities of a third type of bristle disposed in respective first, second, and third sectors.

17. The brush implement according to claim 14, wherein the distal end of the first row of the first type of bristle is adjacent to the central portion of the second row of the first type of bristle; wherein the distal end of the second row of the first type of bristle is adjacent to the central portion of the third row of the first type of bristle; and wherein the distal end of the third row of the first type of bristle is adjacent to the central portion of the first row of the first type of bristle.

18. The brush implement according to claim 17, wherein the portion of bristles of the first type of bristle that forms the outer perimeter is comprised entirely from respective portions of the bristles of the first, second, and third rows.

* * * * *